(12) United States Patent
Huang et al.

(10) Patent No.: US 11,481,557 B2
(45) Date of Patent: Oct. 25, 2022

(54) CLINICAL TERMINOLOGY MAPPING WITH NATURAL LANGUAGE PROCESSING

(71) Applicant: VVC HOLDING CORPORATION, Seattle, WA (US)

(72) Inventors: Wei Huang, Bellevue, WA (US); Eric Wu, Mukilteo, WA (US); Aftab Hassan, Seattle, WA (US); Jau-Huei Lin, Portland, OR (US)

(73) Assignee: VVC Holding LLC, Watertown, MA (US)

( * ) Notice: Subject to any disclaimer, the term of this patent is extended or adjusted under 35 U.S.C. 154(b) by 0 days.

(21) Appl. No.: 16/148,685

(22) Filed: Oct. 1, 2018

(65) Prior Publication Data
US 2019/0102380 A1    Apr. 4, 2019

Related U.S. Application Data

(60) Provisional application No. 62/566,069, filed on Sep. 29, 2017.

(51) Int. Cl.
| | |
|---|---|
| *G16H 10/00* | (2018.01) |
| *G06F 40/30* | (2020.01) |
| *G06F 16/28* | (2019.01) |
| *G06F 16/901* | (2019.01) |

(52) U.S. Cl.
CPC ............ *G06F 40/30* (2020.01); *G06F 16/288* (2019.01); *G06F 16/9024* (2019.01); *G16H 10/00* (2018.01)

(58) Field of Classification Search
CPC ............................... G16H 10/00; G06F 19/32
See application file for complete search history.

(56) References Cited

U.S. PATENT DOCUMENTS

| | | | |
|---|---|---|---|
| 6,915,254 B1 | 7/2005 | Heinze et al. | |
| 7,610,192 B1 | 10/2009 | Jamieson | |
| 8,260,779 B2 | 9/2012 | Hudgins et al. | |
| 8,346,804 B2 | 1/2013 | Philips | |
| 8,639,522 B2 | 1/2014 | Pathria et al. | |
| 9,069,768 B1* | 6/2015 | Sampson | G06V 30/418 |
| 2010/0082333 A1* | 4/2010 | Al-Shammari | G06F 16/3335 704/10 |
| 2012/0110016 A1* | 5/2012 | Phillips | G06F 16/285 707/E17.014 |
| 2013/0332466 A1* | 12/2013 | Bornea | G06F 16/951 707/E17.084 |
| 2014/0095205 A1* | 4/2014 | Farooq | G16H 10/60 705/3 |
| 2016/0019356 A1 | 1/2016 | Martin et al. | |

* cited by examiner

*Primary Examiner* — Feng-Tzer Tzeng
(74) *Attorney, Agent, or Firm* — GTC Law Group PC & Affiliates (57) ABSTRACT

Methods and systems are provided for mapping clinical terminology with natural language processing. In one embodiment, an example method includes generating a word relationship graph for a plurality of mappings between a first code set and a second code set, receiving a first code of the first code set, and automatically mapping a second code of the second code set to the first code based on the word relationship graph. In this way, seemingly different code descriptions from different medical vocabularies may be automatically mapped to each other with reduced processing and reduced human intervention.

12 Claims, 12 Drawing Sheets

```
In [8]: words = ['diabetes', 'mellitus', 'family', 'history']
        similar_terms(model, words, df)
```

Out[8]:

| label | score | text |
|---|---|---|
| 2303 | 0.885608 | diabetes mellitus, family hx |
| 29126 | 0.861230 | diabetes mellitus, family hx, father |
| 32181 | 0.860112 | diabetes mellitus, family hx, comments |
| 202284 | 0.831026 | DIABETES MELLITUS, FAMILY HX, SISTER |
| 202283 | 0.830792 | DIABETES MELLITUS, FAMILY HX, BROTHER |

CLINICAL TERMINOLOGY MAPPING WITH NATURAL LANGUAGE PROCESSING

RELATED APPLICATION

This patent claims the benefit of U.S. Provisional Application Ser. No. 62/566,069, entitled "Clinical Terminology Mapping with Natural Language Processing," which was filed on Sep. 29, 2017. U.S. Provisional Application Ser. No. 62/566,069 is hereby incorporated herein by reference in its entirety for all purposes.

FIELD

Embodiments or examples of the subject matter disclosed herein relate to building and maintaining medical vocabularies, and more particularly, to mapping clinical terminology with natural language processing.

BACKGROUND

Medical text plays an important role in the delivery of healthcare. Using medical text, medical concepts and information can be exchanged using a variety of documents including progress notes, discharge summaries, prescriptions, procedure reports, and so on. Medical terminology is voluminous, fragmented, and complex. Multiple standards bodies (e.g., Health Level Seven (HL7), World Health Organization (WHO), etc.) make contributions to categorizing and publishing medical vocabularies (e.g., Systematized Nomenclature of Human and Veterinary Medicine (SNOMED), International Classification of Diseases (ICD), Logical Observation Identifier Names and Codes (LOINC), etc.) across multiple healthcare domains (e.g., medical procedures, problem lists, laboratory, etc.). In developing clinical information systems, data collection can be driven via a controlled medical vocabulary (CMV) that spans multiple organizations and source terminologies. The CMV can be continuously updated and is able to grow and evolve with the growing list of codes and terms.

In many cases, mapping between terminologies has been accomplished for common terminologies that have overlapping information domains. These mappings are made available by government agencies, healthcare providers, and third-party content providers. Most approaches to managing a CMV rely on mapping rules and use of human intervention of terminology engineers or medical coders to understand differences across source vocabularies, to rationalize the organization of data (via hierarchies and relationships), to identify differences in granularity, and to map between codes and synonyms where there is overlap. This process requires a large amount of manpower to maintain an updated vocabulary and is especially burdensome when implementing new systems in an established healthcare organization with an abundance of systems and proprietary codes and synonyms. Combined with internationalization and a desire to share data across healthcare organizations, the problem quickly becomes unmanageable. For this reason, many healthcare IT providers have created their own proprietary codes, relationships, terms and picklists which remain unintegrated with other systems and terminologies.

BRIEF DESCRIPTION

In one embodiment, a method includes generating a word relationship graph for a plurality of mappings between a first code set and a second code set, receiving a first code of the first code set, and automatically mapping a second code of the second code set to the first code based on the word relationship graph. In this way, seemingly different code descriptions from different medical vocabularies may be automatically mapped to each other with minimal processing and minimal human intervention.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

As used herein, the terms "system," "unit," "module," "engine," etc., may include a hardware and/or software system that operates to perform one or more functions. For example, a module, unit, or system may include a computer processor, controller, and/or other logic-based device that performs operations based on instructions stored on a tangible and non-transitory computer readable storage medium, such as a computer memory. Alternatively, a module, unit, engine, or system may include a hard-wired device that performs operations based on hard-wired logic of the device. Various modules, units, engines, and/or systems shown in the attached figures may represent the hardware that operates based on software or hardwired instructions, the software that directs hardware to perform the operations, or a combination thereof.

The following description relates to various examples of building and maintaining medical vocabularies. In particular, systems and methods are provided for mapping clinical terminology with natural language processing. A method for automatically mapping a code in a first code set to code in a second code set, such as the method depicted in FIG. 1, may include generating a word relationship graph and mapping a given code of the first code set to the second code set based on the word relationship graph. A method for generating a word relationship graph, such as the method depicted in FIG. 2, may include graphically linking non-identical words in pre-mapped codes. A method for automatically mapping a given code to a code in a second code set, such as the method depicted in FIG. 3, may include calculating a Jaccard similarity of the given code to each code in the second code set. The methods described herein perform well compared to methods without semantic linking or Jaccard similarity calculations, as illustrated by FIG. 4. The methods described herein may be implemented as executable instructions in a processor system, such as the system depicted in FIG. 5.

A process called crosswalking is used to translate from one code set to another. Crosswalking means mapping or translating a code from one set to another. As described further herein, a system for automatic crosswalking of medical terminology may perform mapping by understanding the relationship between the words in the code description, and creating a graph network of their mappings with each other. Such a system may be flexible enough to include or exclude new or different code sets and can adapt to constraints provided by domain experts (e.g., clinicians) to design the graph network.

Figure 1:
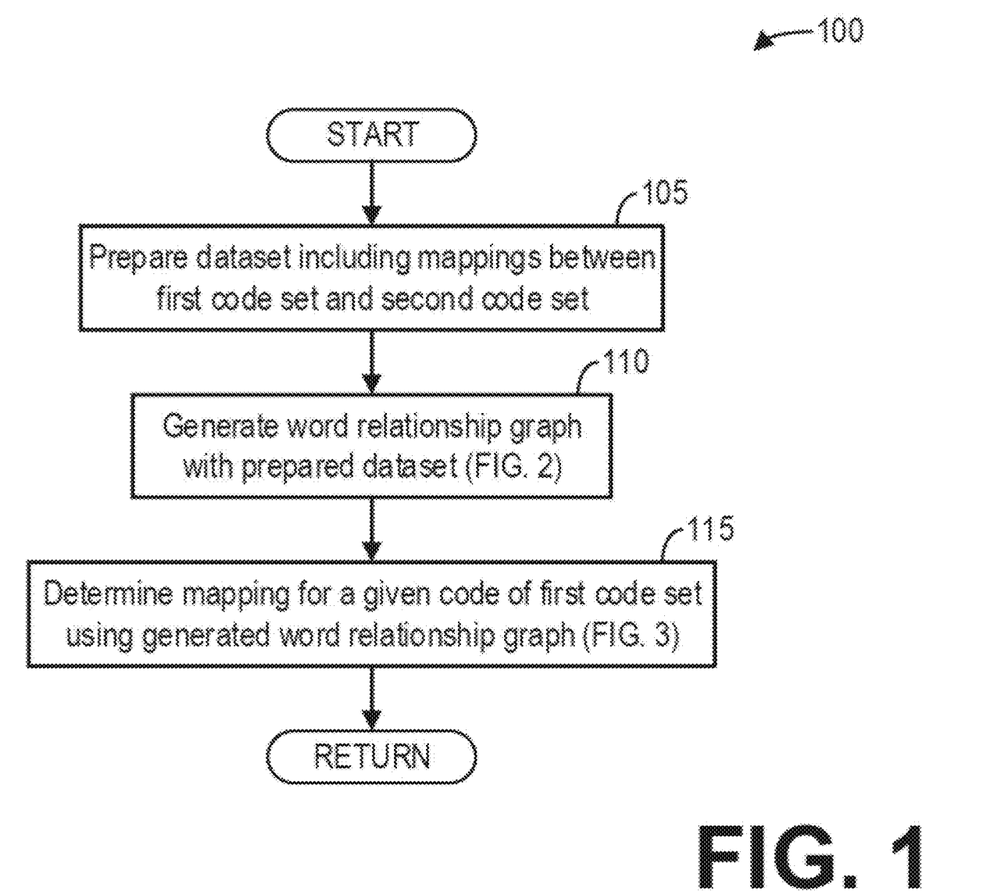
FIG. 1 shows a high-level flow chart illustrating an example method for mapping clinical terminology according to certain examples.

FIG. 1 shows a high-level flow chart illustrating an example method 100 for mapping clinical terminology according to certain examples. In particular, method 100 relates to automatically determining a mapping between codes in different code sets based on a word relationship graph. Method 100 may be implemented as executable instructions in non-transitory memory of a processor system, as described further herein with regard to FIG. 5, though it should be understood that the method may be implemented with other systems and components without departing from the scope of the present disclosure.

Method 100 begins at 105. At 105, method 100 prepares a dataset including mappings between a first code set and a second code set. The first code set and the second code set may include any controlled medical vocabulary or other set of codes for use in clinical information systems, such as a diagnosis code system. A code of the first code set or the second code set includes at least an identification number and a description. The description may include human-readable terms to describe the concept associated with the code.

The dataset may include mappings between codes in the first code set to codes in the second code set. Such mappings may be manually identified by a medical coder or terminology engineer, for example. Depending on the particular code sets, the prepared dataset may include hundreds or thousands of such mappings.

Furthermore, although the method is described with respect to a first code set and a second code set, it should be appreciated that the prepared dataset may include mappings between a plurality of code sets, including a first code set, a second code set, a third code set, a fourth code set, and so on.

Continuing at 110, method 100 uses the prepared dataset to generate a word relationship graph. The word relationship graph links related terminology to each other, thereby enabling a semantic mapping between code sets. For example, a description for a first code in a first code set may use the term "education" while a description for a second code in a second code set may use the term "counseling" to describe the same concept. Mechanically mapping code descriptions to each other may overlook such semantic relationships, and so method 100 identifies such semantic connections to develop the word relationship graph. An example method for creating a word relationship graph based on predetermined mappings between code sets is described further herein with regard to FIG. 2.

At 115, method 100 uses the word relationship graph to determine a mapping for a given code of the first code set. An example method for determining a mapping for a given code using the word relationship graph is described further herein with regard to FIG. 3. Method 100 then returns.

Figure 2:
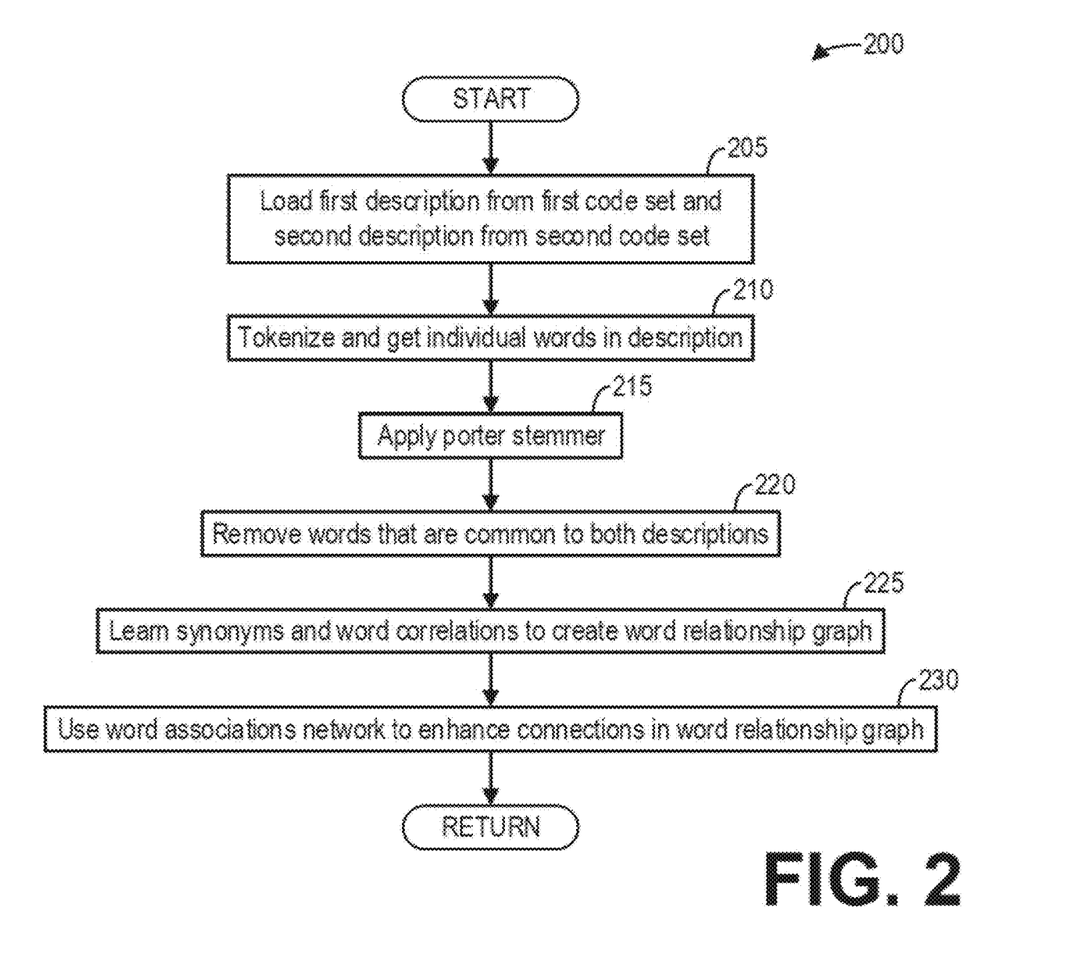
FIG. 2 shows a high-level flow chart illustrating an example method for developing a word relationship graph according to certain examples.

FIG. 2 shows a high-level flow chart illustrating an example method 200 for developing a word relationship graph according to certain examples. In particular, method 200 relates to developing relationships between different words with similar meanings for a given context. Method 200 is described with reference to a single mapping between a first code set and a second code set. Therefore, when implemented as a subroutine for method 100, method 200 may be repeatedly carried out for each mapping between code sets. Method 200 may be implemented as executable instructions in non-transitory memory of a processor system, such as the processor system described further herein with regard to FIG. 5, though it should be appreciated that the method may be implemented with other systems and/or components without departing from the scope of the present disclosure.

Method 200 begins at 205. At 205, method 200 loads a first description from a first code set and a second description from a second code set. The descriptions may be loaded into local memory for processing. As an illustrative example, the table below includes two codes from different code sets that a medical coder may manually map to each other. Specifically, the table includes a first code "2487" from a first code set "OBS" with a first description "Diet Counsel," as well as a second code "424753004" from a second code set "SNOMEDCT" with a second description "Dietary management education guidance and procedure."

| Code | Description |
| --- | --- |
| 2487 (OBS) | Diet Counsel |
| 424753004 (SNOMEDCT) | Dietary management education guidance and procedure |

At 210, method 200 tokenizes and retrieves individual words in the descriptions. Tokenizing the descriptions includes splitting each description from a string into a list of individual tokens or words. As an illustrative example, the first description "Diet Counsel" in the table below when tokenized becomes two tokens: "Diet" and "Counsel." Method 200 further removes stop words from the descriptions. Stop words include the most common words in a language, such as "and", "or", "with", etc. For example, the word "and" is removed from the second description in the table below.

| Code | Description |
| --- | --- |
| 2487 (OBS) | Diet Counsel |
| 424753004 (SNOMEDCT) | Dietary management education guidance and procedure |

At 215, method 200 applies a porter stemmer to each word in the descriptions. A porter stemmer removes common morphological and inflexional endings from words. Applying a porter stemmer to each word reduces inflected words to their word stem. For example, as depicted in the table below, the word "dietary" is reduced to the word stem "diet."

| Code | Description |
| --- | --- |
| 2487 (OBS) | Diet Counsel |
| 424753004 (SNOMEDCT) | Dietary management education guidance and procedure |

At 220, method 200 removes words that are common to both descriptions. For example, as depicted in the table below, the word "diet" occurs in both descriptions, so method 200 removes the word "diet" from both descriptions.

| Code | Description |
| --- | --- |
| 2487 (OBS) | Diet Counsel |
| 424753004 (SNOMEDCT) | Dietary management education guidance and procedure |

At 225, method 200 learns synonyms and word correlations to create a word relationship graph. For the above example, the word "counsel" from the OBS code description is linked to the words "management," "education," "guidance," and "procedure" from the SNOMEDCT code description.

At 230, method 200 uses a word associations network to enhance connections in the word relationship graph. Method 200 then returns.

Figure 3:
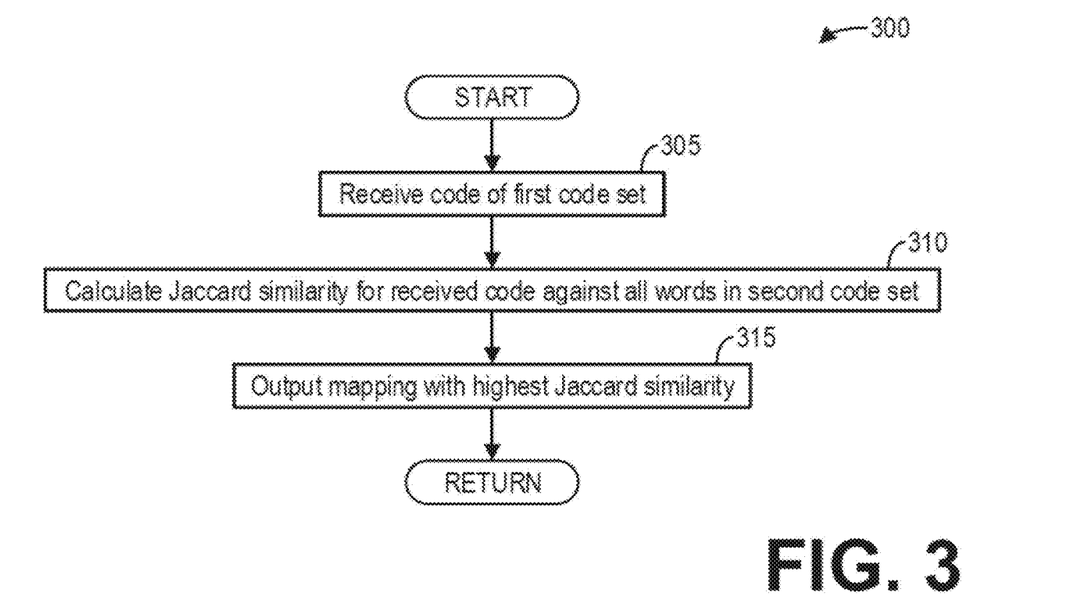
FIG. 3 shows a high-level flow chart illustrating an example method for automatically mapping clinical terminology according to certain examples.
Figure 4:
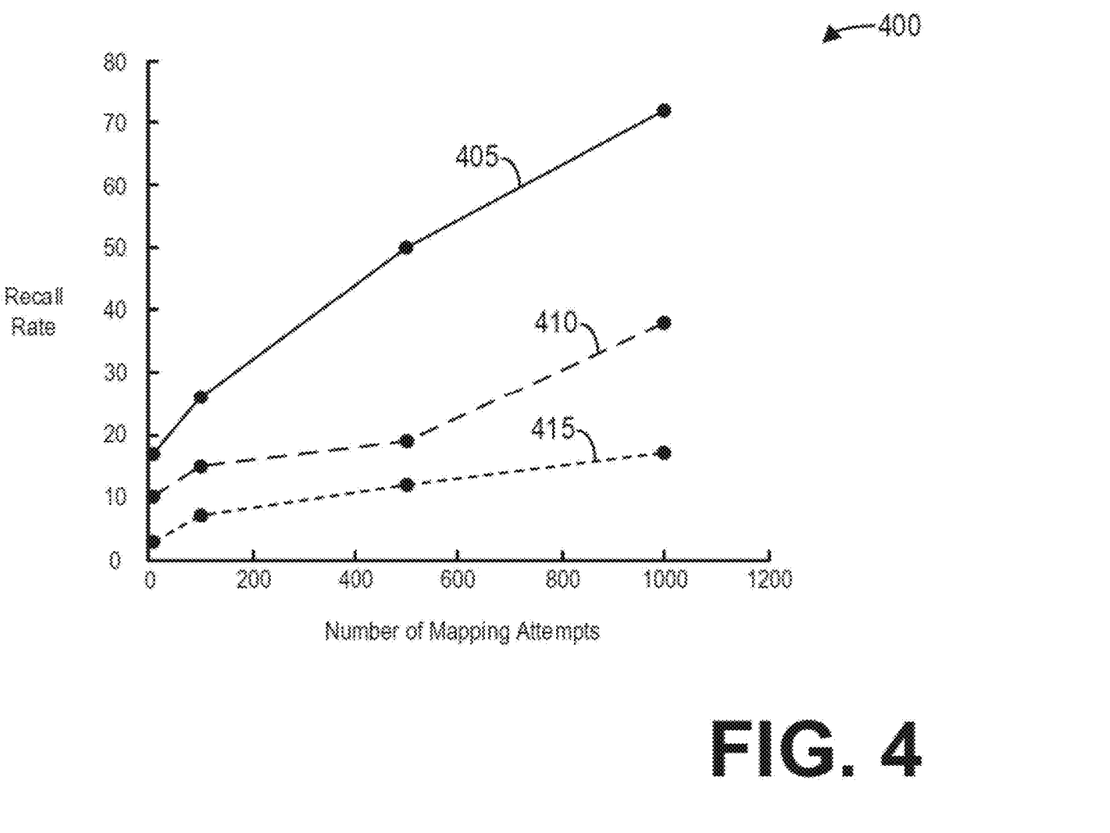
FIG. 4 shows a graph illustrating performance of different approaches for automatic mapping of clinical terminology.

FIG. 3 shows a high-level flow chart illustrating an example method 300 for automatically mapping clinical terminology according to certain examples. In particular, method 300 relates to quantitatively determining which codes of two different code sets are most similar. Method 300 may be implemented as executable instructions in non-transitory memory of a processor system, such as the processor system described further herein with regard to FIG. 5, though it should be appreciated that the method may be implemented with other systems and/or components without departing from the scope of the present disclosure.

Method 300 begins at 305. At 305, method 300 receives a code of the first code set. In some examples, the code may be input manually by a user, for example, via a user interface. In other examples, the code may be automatically input by a processor during execution of another set of executable instructions.

At 310, method 300 calculates a Jaccard similarity for the received code against all codes in the second code set. More specifically, for a set A of words in the description of the received code, the Jaccard similarity J(A, B) of the set A to a set B of words in a description for a code in the second code set is defined as the size of the intersection of the sets divided by the size of the union of the sets:

$$J(A, B) = \frac{|A \cap B|}{|A \cup B|}.$$

Method 300 utilizes the word relationship graph generated by method 200 in order to include synonyms and related concepts or terminology in the calculation of the Jaccard similarity. For example, with reference to the example described with regard to FIG. 2, although the first description includes the term "counsel" and the second description does not include the term "counsel," the value of the Jaccard similarity for the two example codes may be higher because the word relationship graph links the term "counsel" in the first description to the terms "management," "education," "guidance," and "procedure" in the second description. Without the use of the word relationship graph, the Jaccard similarity would be lower because these terms are not mechanically related (i.e., mechanically stemming the term "counsel" does not yield the semantically-related terms "management," "education," "guidance," and "procedure").

After calculating the Jaccard similarity of the set A for the received code against each description in the second code set, method 300 continues to 315. At 315, method 300 outputs the mapping with the highest Jaccard similarity. Method 300 then returns.

FIG. 4 shows a graph 400 illustrating performance of different approaches for automatic mapping of clinical terminology. Graph 400 includes plots 405, 410, and 415 illustrating the recall rate as a function of the number of mapping attempts for different automated mapping methods. Plot 405 depicts the recall rate for the method 100 which includes developing a word relationship graph and calculating a Jaccard similarity. Plot 410 depicts the recall rate for a method that performs the Jaccard similarity calculation without the use of a word relationship graph. Plot 415 depicts the recall rate for a random guess of a mapping.

As depicted by plots 410 and 415, simply calculating the Jaccard similarity without using a word relationship graph is only marginally better than randomly guessing a mapping between two codes. The full method described herein performs substantially better, as depicted by plot 405, especially as the number of mapping attempts is increased and thus the word relationship graph is expanded.

Figure 5:
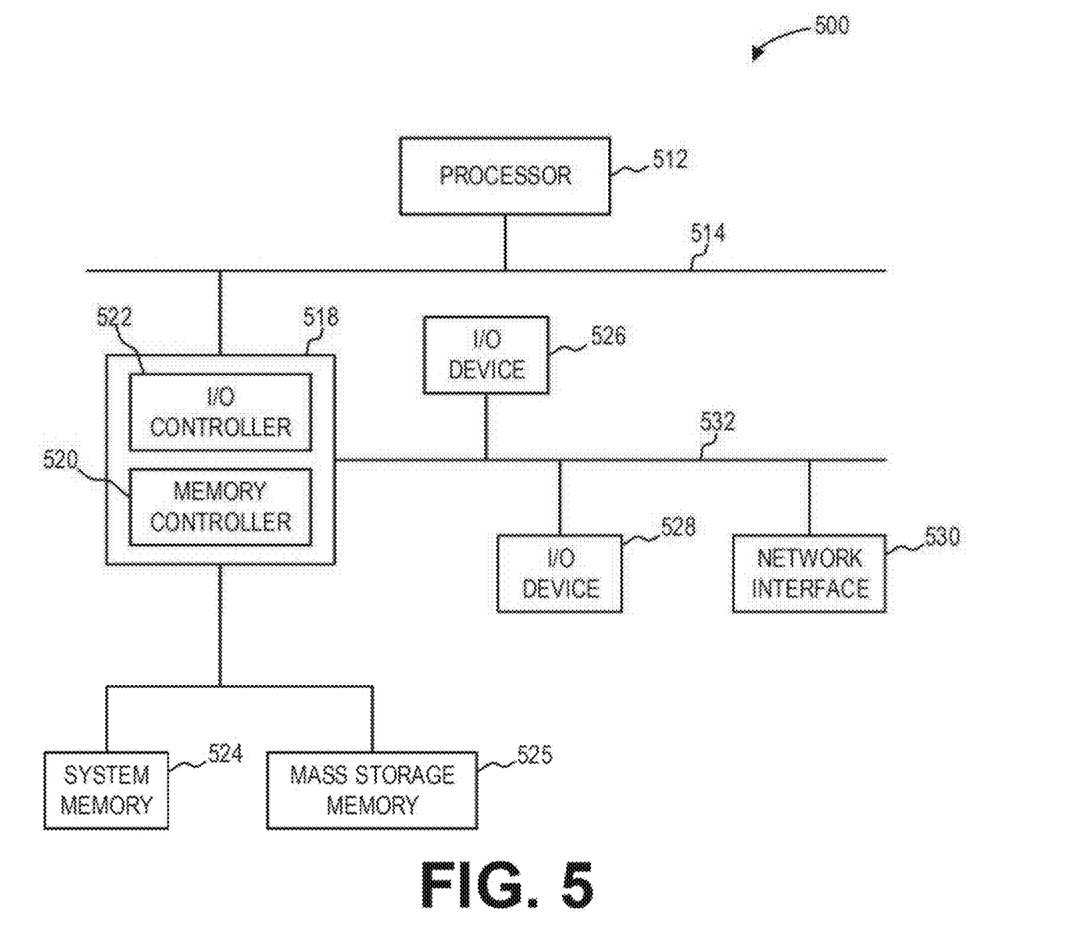
FIG. 5 is a block diagram illustrating an example processor system that may be used to implement systems, apparatuses, and methods described herein.

FIG. 5 is a block diagram of an example processor system 500 that may be used to implement systems, apparatuses, and methods described herein. As shown in FIG. 5, the processor system 500 includes a processor 512 that is coupled to an interconnection bus 514. The processor 512 may be any suitable processor, processing unit, or microprocessor, for example. Although not shown in FIG. 5, the processor system 500 may be a multi-processor system, and, thus, may include one or more additional processors that are identical or similar to the processor 512 and that are communicatively coupled to the interconnection bus 514.

The processor 512 of FIG. 5 is coupled to a chipset 518, which includes a memory controller 520 and an input/output ("I/O") controller 522. As is well known, a chipset typically provides I/O and memory management functions as well as a plurality of general purpose and/or special purpose registers, timers, etc. that are accessible or used by one or more processors coupled to the chipset 518. The memory controller 520 performs functions that enable the processor 512 (or processors if there are multiple processors) to access a system memory 524 and a mass storage memory 525.

The system memory 524 may include any desired type of volatile and/or non-volatile memory such as, for example, static random access memory (SRAM), dynamic random access memory (DRAM), flash memory, read-only memory (ROM), etc. The mass storage memory 525 may include any desired type of mass storage device including hard disk drives, optical drives, tape storage devices, etc.

The I/O controller 522 performs functions that enable the processor 512 to communicate with peripheral input/output ("I/O") devices 526 and 528 and a network interface 530 via an I/O bus 532. The I/O devices 526 and 528 may be any desired type of I/O device such as, for example, a keyboard, a video display or monitor, a mouse, etc. The network interface 530 may be, for example, an Ethernet device, an asynchronous transfer mode ("ATM") device, an 802.11 device, a DSL modem, a cable modem, a cellular modem, etc. that enables the processor system 500 to communicate with another processor system.

While the memory controller 520 and the I/O controller 522 are depicted in FIG. 5 as separate blocks within the chipset 518, the functions performed by these blocks may be integrated within a single semiconductor circuit or may be implemented using two or more separate integrated circuits.

Certain embodiments and/or examples contemplate methods, systems, and computer program products on any machine-readable media to implement functionality described above. Certain embodiments/examples may be implemented using an existing computer processor, or by a special purpose computer processor incorporated for this or another purpose or by a hardwired and/or firmware system, for example.

Some or all of the system, apparatus, and/or article of manufacture components described above, or parts thereof, can be implemented using instructions, code, and/or other software and/or firmware, etc. stored on a machine-accessible or readable medium and executable by, for example, a processor system (e.g., the processor system 500 of FIG. 5). When any of the appended claims are read to cover a purely software and/or firmware implementation, at least one of the components is hereby expressly defined to include a tangible medium such as a memory, DVD, CD, etc. storing the software and/or firmware.

A technical effect of the disclosure is the generation and updating of a word relationship graph that automatically links semantically similar words in different clinical code descriptions. Another technical effect of the disclosure is the automatic mapping of a given code in a first code set to a code in a second code set. Yet another technical effect of the disclosure is the improved performance of automatic crosswalking with minimal human intervention.

In one embodiment, a method comprises generating a word relationship graph for a plurality of mappings between a first code set and a second code set, receiving a first code of the first code set, and automatically mapping a second code of the second code set to the first code based on the word relationship graph.

In a first example of the method, generating the word relationship graph comprises loading a first description of the first code set and a second description of the second code set, removing words common to the first description and the second description, and graphically linking remaining words in the first description to remaining words in the second description, wherein the first description is mapped to the second description. In a second example of the method optionally including the first example, the method further comprises tokenizing the first description and the second description respectively into a first set of words and a second set of words, wherein removing words common to the first description and the second description comprises removing words common to the first set of words and the second set of words. In a third example of the method optionally including one or more of the first and second examples, the method further comprises stemming each word in the first set of words and the second set of words prior to removing words common to the first set of words and the second set of words. In a fourth example of the method optionally including one or more of the first through third examples, generating the word relationship graph comprises graphically linking words in mapped descriptions for each mapping of the plurality of mappings. In a fifth example of the method optionally including one or more of the first through fourth examples, automatically mapping the second code to the first code comprises calculating a similarity of the first code to each code of the second code set. In a sixth example of the method optionally including one or more of the first through fifth examples, calculating the similarity comprises calculating a Jaccard similarity of the first code to each code of the second code set. In a seventh example of the method optionally including one or more of the first through sixth examples, the second code is automatically mapped to the first code responsive to the Jaccard similarity between the first code and the second code being higher than each other calculated Jaccard similarity for the first code. In an eighth example of the method optionally including one or more of the first through seventh examples, automatically mapping the second code of the second code set to the first code based on the word relationship graph comprises calculating the Jaccard similarity of the first code to each code of the second code set based on word relationship graph.

In another embodiment, a method comprises preparing a dataset including mappings between a first code set and a second code set, generating a word relationship graph with the prepared dataset, and determining a mapping for a given code of the first code set using the generated word relationship graph.

In a first example of the method, generating a word relationship graph with the prepared dataset comprises, for each mapping of the mappings: loading a first description of the first code set and a second description of the second code set; tokenizing the first description and the second description respectively into a first set of words and a second set of words; stemming each word of the first set of words and the second set of words to respectively create a first stemmed set of words and a second stemmed set of words; removing words common to the first stemmed set of words and the second stemmed set of words; and graphically linking remaining words of the first stemmed set of words to remaining words of the second stemmed set of words to update the word relationship graph. In a second example of the method optionally including the first example, determining the mapping for the given code of the first code set using the generated word relationship graph comprises calculating a Jaccard similarity of the given code against each code of the second code set. In a third example of the method optionally including one or more of the first and second examples, the method further comprises outputting a mapping between the given code and a second code of the second code set, wherein the Jaccard similarity between the given code and the second code is a highest value for the Jaccard similarity of the given code. In a fourth example of the method optionally including one or more of the first through third examples, at least one word in the given code and at least one word of the second code are considered similar based on the word relationship graph.

In yet another embodiment, a system comprises a processor, a computer-readable storage medium, and executable program instructions embodied in the computer-readable storage medium that, when executed by the processor, cause the processor to: generate a word relationship graph for a plurality of mappings between a first code set and a second code set; receive a first code of the first code set; and automatically map a second code of the second code set to the first code based on the word relationship graph.

In a first example of the system, generating the word relationship graph comprises loading a first description of the first code set and a second description of the second code set, removing words common to the first description and the second description, and graphically linking remaining words in the first description to remaining words in the second description, wherein the first description is mapped to the second description. In a second example of the system optionally including the first example, generating the word relationship graph comprises graphically linking words in mapped descriptions for each mapping of the plurality of mappings. In a third example of the system optionally including one or more of the first and second examples, automatically mapping the second code to the first code comprises calculating a similarity of the first code to each code of the second code set. In a fourth example of the system optionally including one or more of the first through third examples, calculating the similarity comprises calculating a Jaccard similarity of the first code to each code of the second code set. In a fifth example of the system optionally including one or more of the first through fourth examples, automatically mapping the second code of the second code set to the first code based on the word relationship graph comprises calculating the Jaccard similarity of the first code to each code of the second code set based on word relationship graph.

Figure 6:
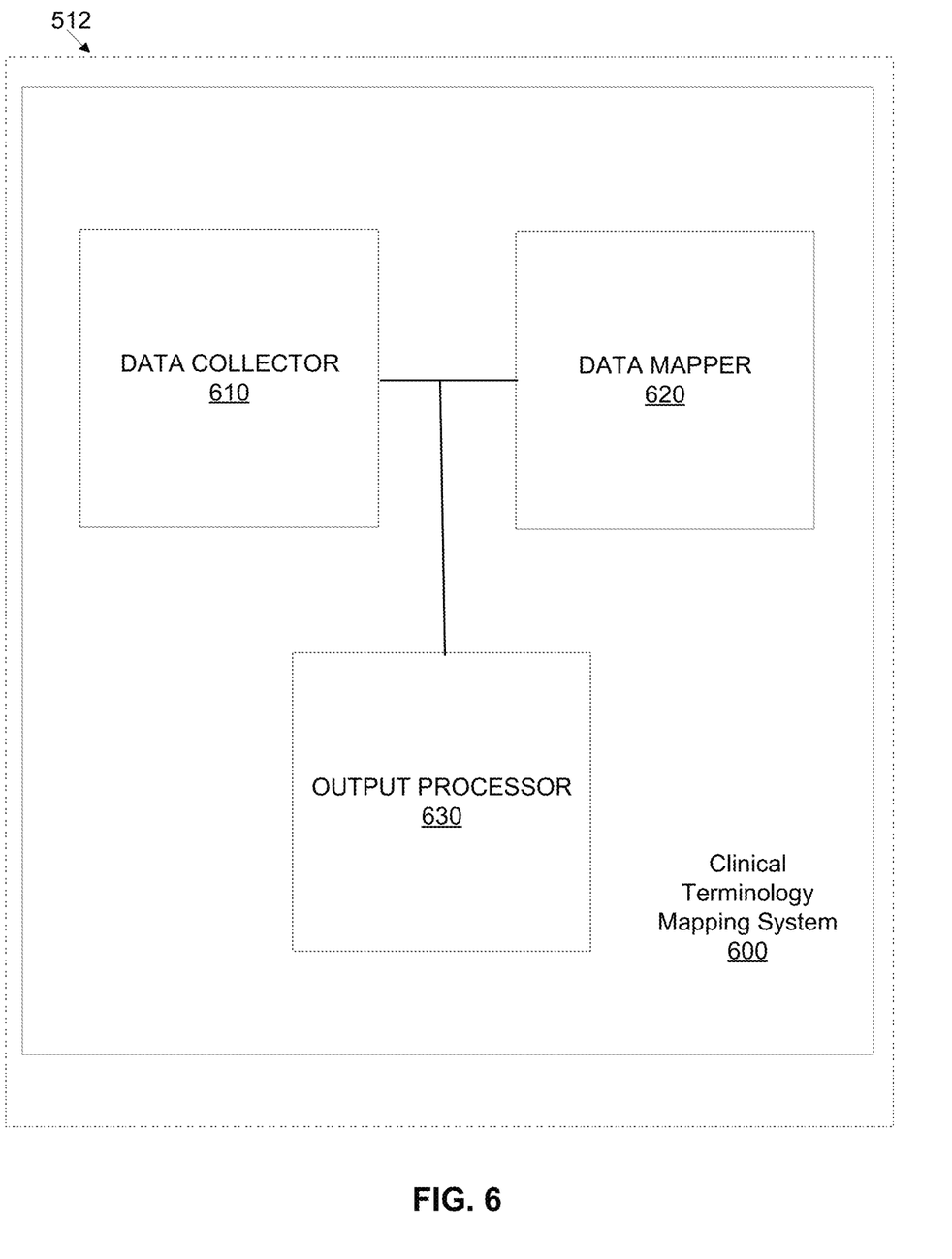
FIG. 6 illustrates an example clinical terminology mapping system according to certain examples.

FIG. 6 illustrates an example clinical terminology mapping system 600. The example system 600 can be implemented using the example processor 512 of FIG. 5, for example. As shown in FIG. 6, the example system 600 includes a data collector 610, a data mapper 620, and an output processor 630. The example data collector 610 gathers data from one or more documents and/or records and parses/analyzes the data to identify content (e.g., words, phrases, relationships, etc.). The example data mapper 620 processes the gathered, parsed data to apply one or more mappings, processing, and/or reduction to the data, such as "enhanced bag of words", "word embeddings with deep learning", etc. The example output processor 630 processes the mapped data to generate one or more outputs. Using the data mapper 620, the output processor 630 can generate matched output between a search string and a target terminology corpus with improved accuracy and performance, for example.

Enhanced Bag of Words

Traditionally, search engine and database technologies use string matching mechanism to find targeted similar documents for an entered search term. That relies on the string similarity between the search term and the document. For example, if the user types "hypertension", the search engine may return "hypertensive nephropathy" or "antihypertensive agent" but may not return "high blood pressure". Because, the latter requires the understanding of the closeness of meaning between "hypertension" and "high blood pressure" despite their strings may not closely matched. This is the challenge of semantic search.

The challenge of semantic similarity can be overcome by identifying synonyms for search engine. However, the identification and maintenance of synonyms can be a labor-intensive work. The "enhanced bag of words" augments the traditional workflow with learning synonyms and word correlation to create a word relationship graph in the data mapper 620. The synonyms and word correlation are learned from existing mappings so as to not require extra manual resource. For example, the data mapper 620 can process an OBS to SNOMED mapping and/or other created mapping to learn the word relationship, etc.

Figure 7:
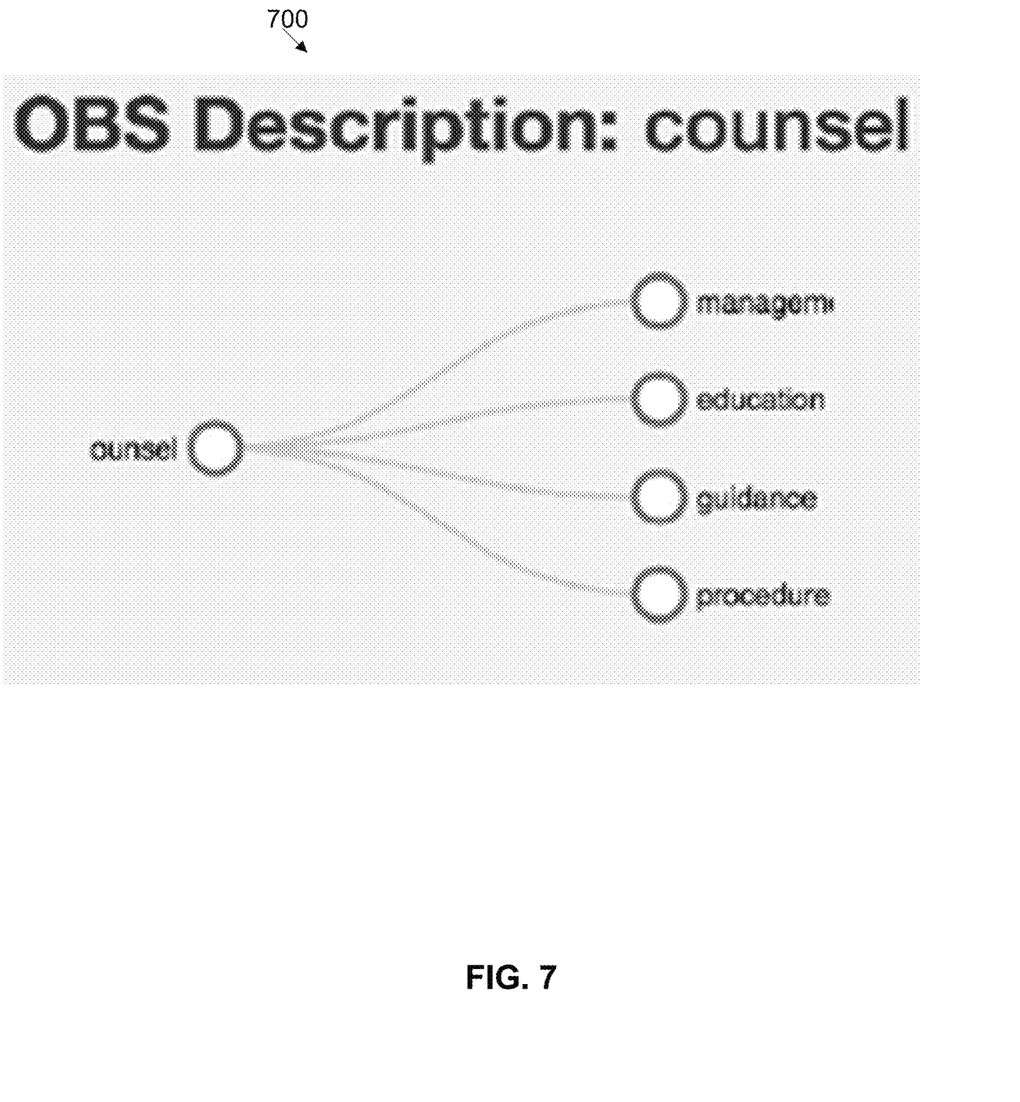
FIG. 7 shows an example word relationship graph according to certain examples.
Figure 8:
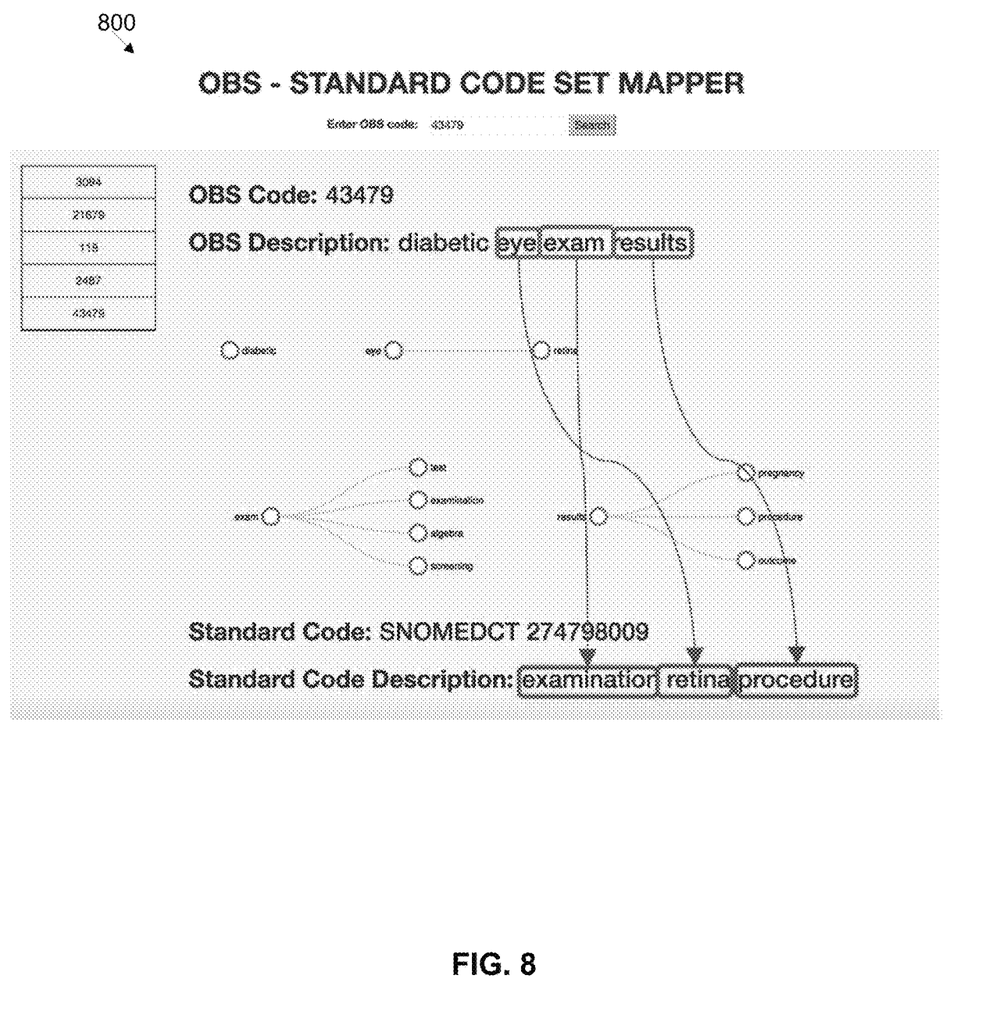
FIG. 8 shows an example standard code set mapper according to certain examples.

The "enhanced bag of words" method provides an augmented workflow with a synonym learning mechanism including tokenizing, stemming, stop word removal, etc. In addition, the method also learns semantically close words from human expert identified mapped documents and stores the relationship in word relationship graph. For example, human experts may identify "diet counsel" is equivalent to "dietary management education guidance and counseling procedure". Based on the human-identified association, a word relationship graph maintains counsel-management, counsel-education, counsel-guidance, and counsel-procedure relationship as potential synonyms. The word relationship graph, such as shown in the example of FIG. 7, mains relationships between words that can be used in code mappings. The learned relationship will then be used in search phase as to identifying similarity, such as shown in the example OBS standard code set mapper of FIG. 8. As shown in the example of FIG. 8, an OBS code and OBS description can be mapped to a standard SNOMEDCT code and standard code description through mappings for diabetic, eye, exam, and results.

Word Embeddings with Deep Learning

The word embeddings approach is following a paradigm different from "bag of words" type of search engine. The bag-of-words approaches are usually based on word matching with variations—stemming, stop words, or synonyms—with calculated weight on indexing or searching phase. The matching is basically string matching. The main difference in word embeddings approach vs bag-of-word is matching for word embeddings is vector-based.

Word embeddings approaches create vectors, e.g., [1.2, −0.3, 0, . . . ] for each document in the corpus, which is the collection of target documents for search. During a training phase (equivalent to an indexing phase of traditional search engine approaches), a deep learning algorithm learns a vectorization model from the corpus. During an evaluation phase (equivalent to a query phase of traditional search engine approaches), the same vectorization model applies to the query string and generates a query vector. The matching compares the query vector and all vectors in the corpus. The (cosine of) angle between two vectors is then used as the measurement of similarity of two documents. For example, if the angle of two vectors is 0 degree, then the similarity score will be 1; if the angle is 90 degree, then the similarity is 0.

Deep learning algorithms such as word2vec, doc2vec, etc., can be used to process word embeddings. However, certain examples apply deep learning algorithms to word embeddings in patient medical and/or other healthcare data with a domain specific terminology, such as LOINC or SNOMED standard terminology, or GE-proprietary OBS terminology.

The application of this method to the domain-specific terminologies has special implications. A domain-specific terminology usually comprehensively covers concepts within that domain. The terminology has several relevant fields, e.g., name, descriptions, keywords, parents, etc. These can help create a well-representative vector space. In addition, when learning the vectorization model with all these relevant fields, the searching can achieve certain degree of semantic matching because synonym conditions are implied in these context fields, for examples, synonyms most likely have very similar keyword sets.

Figure 9:
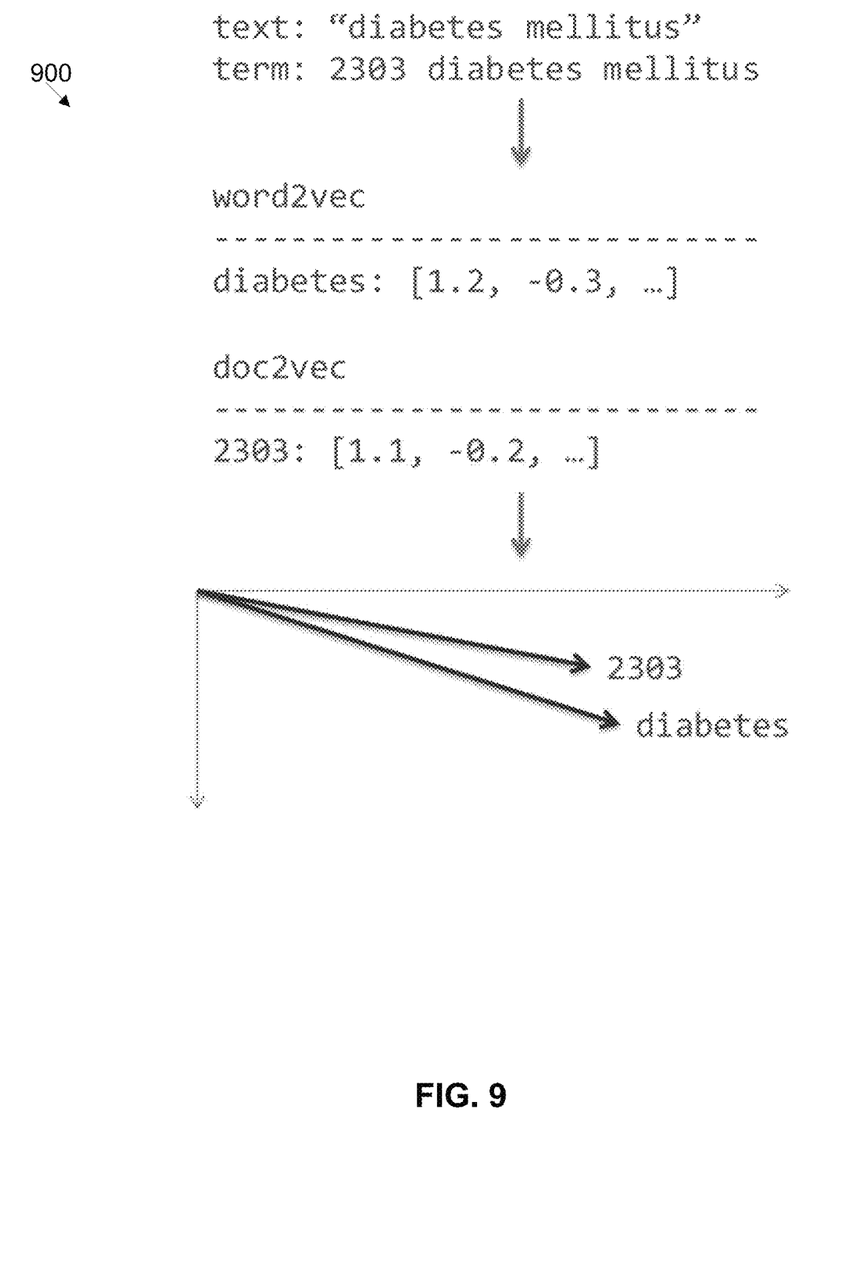
FIG. 9 illustrates an example vectorization according to certain examples.
Figure 10:
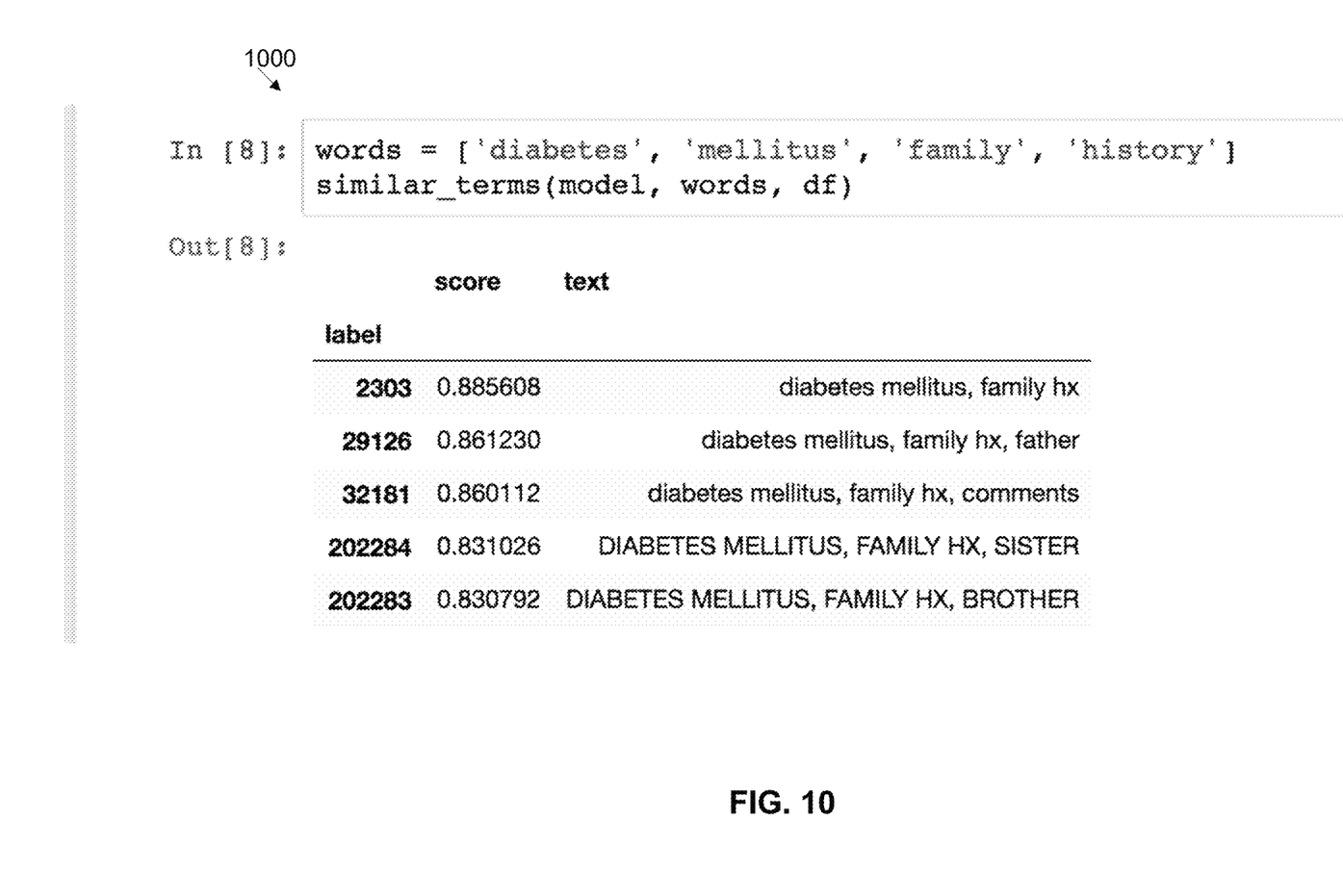
FIG. 10 shows a comparison between a query vector and corpus vectors as well as a ranking of similar documents according to certain examples.
Figure 11:
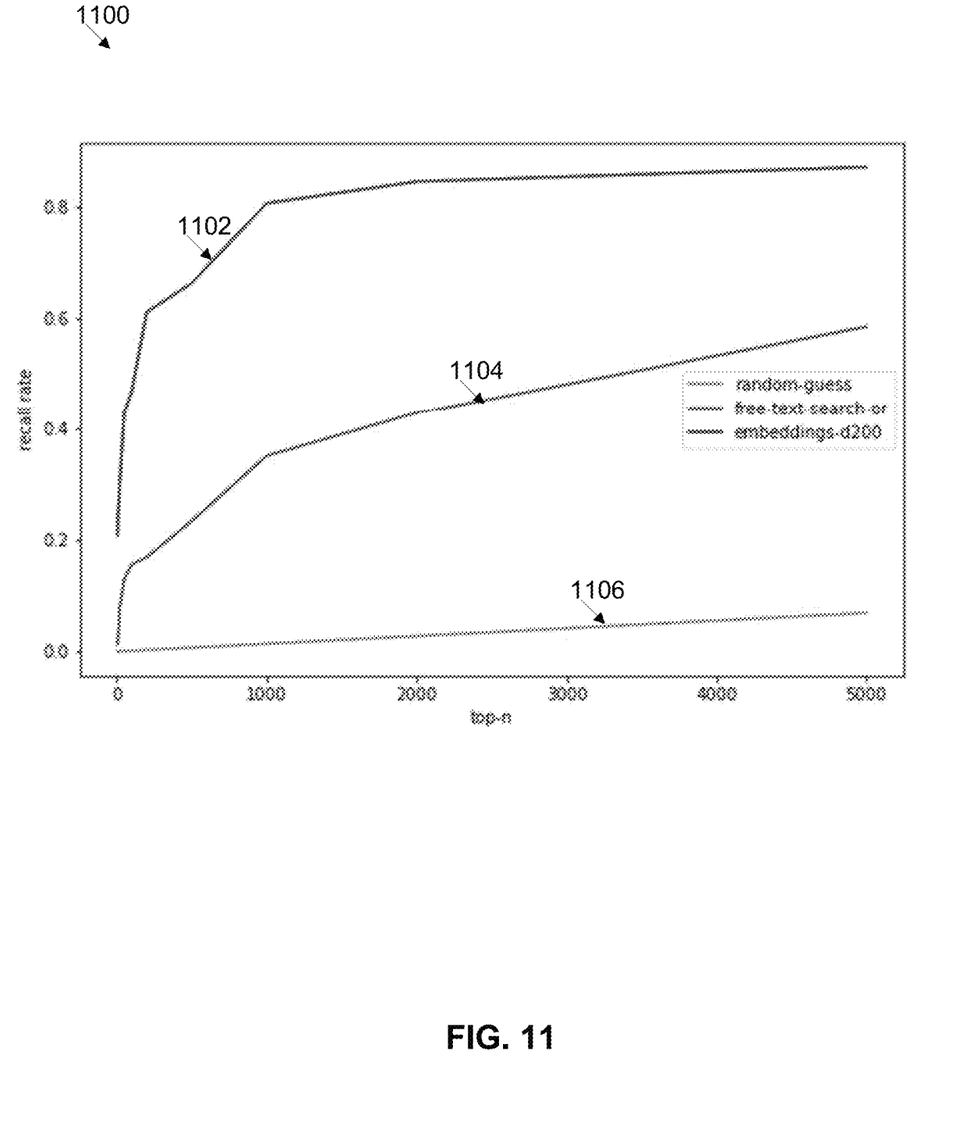
FIG. 11 illustrates a graph showing a performance result of applying word embeddings with deep learning according to certain examples.

FIG. 9 illustrates an example vectorization 900 of "diabetes mellitus" to vector [1.1, –0.3, . . . ]. For example, a set of 70,000 OBS terms (name, description, keywords, etc.) can be vectorized into a set of 70,000 vectors and vectorization algorithms using deep learning. FIG. 10 shows a comparison 1000 between a query vector and the corpus vectors and lists the most similar documents by the rank of scores. FIG. 11 illustrates a graph showing a performance result 1100 of applying word embeddings with deep learning 1102 rather than a free text search 1104 or random guess 1106.

Figure 12:
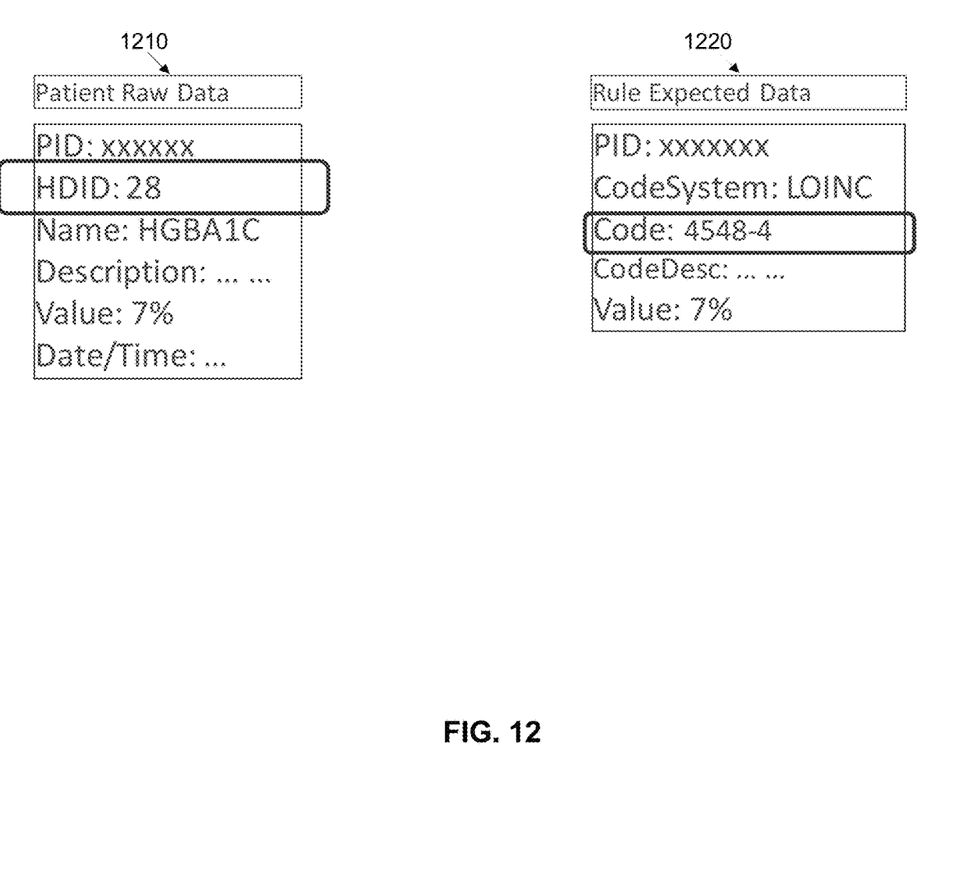
FIG. 12 illustrates an example of patient raw data versus rule-expected data to be processed according to certain examples.

Thus, certain examples provide automatic mapping of codes and/or terms from one terminology to another terminology. Certain examples provide fuzzy semantic search in clinical areas including an entire patient chart. Certain examples identify and reconcile discrepancies, inaccuracies, and/or incomplete translations when mapping between code sets. Certain examples provide a flexible mapping framework to perform mapping by understanding the relationship between words in the code description and creating a graph network of mappings with each other. The framework is flexible enough to include or exclude new or different code sets and can adapt to constraints provided by domain experts (e.g., clinicians, etc.) to generate the graph network. Certain examples enable extraction of clinical concepts from freetext, such as a radiology report, physician note, etc., for incorporation into a medical record and/or further processing. Thus, patient data from OBS code sets can be mapped to patient data in value set codes, which can be distributed to a rules engine, analytics, health information exchange, etc. FIG. 12 illustrates an example of patient raw data 1210 and rule-expected data 1220 to be processed by a rules engine, etc. The data mapper 620 can transform the patient raw data 1210 to the rule-expected data 1220 for output by the output processor 630 for processing by the rules engine, storage in an electronic medical record, aggregation in a health information exchange, etc.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method comprising:
generating a word relationship graph for a plurality of mappings between a first code set and a second code set;
receiving a first code of the first code set; and
automatically mapping a second code of the second code set to the first code based on the word relationship graph by calculating a Jaccard similarity of the first code to each code of the second code set;
wherein generating the word relationship graph includes loading a first description of the first code set and a second description of the second code set, removing words common between the first description and the second description, and graphically linking remaining words in the first description to remaining words in the second description, wherein the first description is mapped to the second description.

2. The method of claim 1, further including tokenizing the first description and the second description respectively into a first set of words and a second set of words, wherein removing words common between the first description and the second description includes removing words common between the first set of words and the second set of words.

3. The method of claim 2, further including stemming each word in the first set of words and the second set of words prior to removing words common between the first set of words and the second set of words.

4. The method of claim 1, wherein generating the word relationship graph includes graphically linking words in mapped descriptions for each mapping of the plurality of mappings.

5. The method of claim 1, wherein the second code is automatically mapped to the first code responsive to the Jaccard similarity between the first code and the second code being higher than each other calculated Jaccard similarity for the first code.

6. The method of claim 1, wherein automatically mapping the second code of the second code set to the first code based on the word relationship graph includes calculating the Jaccard similarity of the first code to each code of the second code set based on word relationship graph.

7. A method comprising:
preparing a dataset including mappings between a first code set and a second code set;
generating a word relationship graph with the prepared dataset; and
determining a mapping for a given code of the first code set using the generated word relationship graph by calculating a Jaccard similarity of the given code against each code of the second code set;
wherein generating a word relationship graph with the prepared dataset comprises, for each mapping of the mappings:
loading a first description of the first code set and a second description of the second code set;
tokenizing the first description and the second description respectively into a first set of words and a second set of words;
stemming each word of the first set of words and the second set of words to respectively create a first stemmed set of words and a second stemmed set of words;
determining a shared set of words that occur in both the first stemmed set of words and in the second stemmed set of words;
removing members of the shared set of words from both the first stemmed set of words and the second stemmed set of words; and
graphically linking remaining words of the first stemmed set of words to remaining words of the second stemmed set of words to update the word relationship graph.

8. The method of claim 7, further including outputting a mapping between the given code and a second code of the second code set, wherein the Jaccard similarity between the given code and the second code is a highest value for the Jaccard similarity of the given code.

9. The method of claim 8, wherein at least one word in the given code and at least one word of the second code are considered similar based on the word relationship graph.

10. A system comprising:
a processor;
a computer-readable storage medium; and
executable program instructions embodied in the computer-readable storage medium that, when executed by the processor, cause the processor to:
generate a word relationship graph for a plurality of mappings between a first code set and a second code set by calculating a Jaccard similarity of the first code to each code of the second code set;
receive a first code of the first code set; and
automatically map a second code of the second code set to the first code based on the word relationship graph;
wherein generating the word relationship graph includes loading a first description of the first code set and a second description of the second code set, removing words occurring in both the first description and in the second description, and graphically linking remaining words in the first description to remaining words in the second description, wherein the first description is mapped to the second description.

11. The system of claim 10, wherein generating the word relationship graph includes graphically linking words in mapped descriptions for each mapping of the plurality of mappings.

12. The system of claim 10, wherein automatically mapping the second code of the second code set to the first code based on the word relationship graph includes calculating the Jaccard similarity of the first code to each code of the second code set based on word relationship graph.

* * * * *